US006953574B2

United States Patent
Sobol et al.

(10) Patent No.: US 6,953,574 B2
(45) Date of Patent: Oct. 11, 2005

(54) METHOD FOR PRODUCING A FERMENTED HYDROLYZED MEDIUM CONTAINING MICROORGANISMS

(75) Inventors: Constantin Vladimirovich Sobol, St.-Petersburg (RU); Yuzefa Tsezarevna Sobol, St.-Petersburg (RU)

(73) Assignee: Technology Commercialization, Inc., New York, NY (US)

( * ) Notice: Subject to any disclaimer, the term of this patent is extended or adjusted under 35 U.S.C. 154(b) by 181 days.

(21) Appl. No.: 10/178,447

(22) Filed: Jun. 21, 2002

(65) Prior Publication Data

US 2003/0235559 A1 Dec. 25, 2003

(51) Int. Cl.$^7$ .................. A01N 63/00; A01N 43/04; A61K 35/78; C12P 1/00; C07H 3/00
(52) U.S. Cl. .............. 424/93.45; 424/93.1; 424/93.44; 424/439; 424/725; 424/774; 426/34; 426/49; 426/61; 435/41; 435/42; 435/68.1; 435/71.2; 435/243; 435/252.4; 435/252.9; 435/253.9; 514/53; 514/54; 536/124; 536/128
(58) Field of Search ................ 424/93.1, 725, 424/774; 435/41, 42, 68.1, 71.2, 243, 252.4, 252.9, 253.9; 514/53, 54; 536/124, 128

(56) References Cited

U.S. PATENT DOCUMENTS

| | | | |
|---|---|---|---|
| 4,110,477 A | * | 8/1978 | Naruse et al. ............ 426/46 |
| 4,298,620 A | | 11/1981 | Hagiwara |
| 5,292,511 A | | 3/1994 | Kim |
| 5,308,615 A | | 5/1994 | DeLoach |
| 5,587,313 A | | 12/1996 | Weiner |
| 5,620,877 A | | 4/1997 | Farone et al. |
| 5,702,927 A | | 12/1997 | Murofushi |
| 5,908,622 A | | 6/1999 | Barclay |
| 6,030,650 A | * | 2/2000 | Kamarei ............... 426/72 |
| 6,046,022 A | | 4/2000 | Zhang |
| 6,054,148 A | | 4/2000 | Rust et al. |
| 6,228,358 B1 | | 5/2001 | Toba |
| 6,270,811 B1 | | 8/2001 | Fregonese |

FOREIGN PATENT DOCUMENTS

| | | |
|---|---|---|
| RU | 282052 | 12/1971 |
| RU | 291545 | 4/1981 |
| WO | WO 97/29644 | 8/1997 |
| WO | WO 00/75284 | 12/2000 |

OTHER PUBLICATIONS

Oxoid Manual. The Oxoid Manual of Culture Media, Ingredients and Other Laboratory Services. 1982. Fifth Edition, Oxoid Limited, Basingstoke, Hampshire, U.K., p. 237.*
Norm F. Olson. Measuring Cheese Acidity. *UW Dairy Pipeline*, vol. 2, No. 3, 1990, pp.1–8.

* cited by examiner

*Primary Examiner*—David M. Naff
*Assistant Examiner*—Kailash C. Srivastava
(74) *Attorney, Agent, or Firm*—Boris Leschinsky

(57) ABSTRACT

A method of producing a hydrolyzed fermented medium containing microorganisms includes providing at least one solid plant product reduced to small pieces and mixed with sugar and biocompatible liquid such as milk for fermentation at a temperature of between 35 and 58 degrees C. until the acidity of the medium reaches the range of 300 to 900 in Terner degrees. Alternatively, the medium is prepared by mixing in predetermined amounts of sprouted grains, biocompatible liquid inoculated with at least one of a variety of non-pathogenic microorganisms, vegetables, fruits, berries, high protein products, herbs, sugar, and a chemical element such as potassium. The mixture is then fermented at a selected temperature for a specified length of time to reach high acidity and high concentration of products of bacterial metabolism. A liquid phase is separated from a solid sediment phase and can be used to treat a wide variety of diseases.

14 Claims, No Drawings

METHOD FOR PRODUCING A FERMENTED HYDROLYZED MEDIUM CONTAINING MICROORGANISMS

FIELD OF THE INVENTION

The present invention relates to a hydrolyzed medium made by fermentation with non-pathogenic microorganisms and to the process of manufacturing and use thereof. More particularly it relates to the production of sour milk based hydrolysate, which includes the fermentation of various food ingredients and plants using various non-pathogenic bacteria/yeast ingredients and some food-grade fungi in milk/whey or water, in its liquid form or solid dried form.

The medium produced by this method has physiologically beneficial effects and therapeutic activity against various diseases, including several life-threatening conditions. It can also be used in cosmetic industry for improving skin and food industry for production of dairy products, to accelerate cheese ripening and maturation, to improve the cultivation and long-term storage/preservation of viable Lactobacilli, acetic, propionic and bifidobacteria in their most active state.

In animal husbandry, the medium of the invention can be used as a feed supplement, for prevention and treatment of infection diseases, for growth promotion, to improve feed conversion, and to increase the yield of useful products, such as milk and eggs.

BACKGROUND OF THE INVENTION

The art of fermentation, i.e. the transformation of organic compounds with the aid of enzymes produced by microorganisms, is well known. Microbial activity is fairly well understood in the food industry. Fermentation is used widely in the production of alcoholic beverages, dairy products and some Oriental fermented foods, especially in tropical climates.

About one hundred years ago, Metchnikoff developed a theory that the ingestion of soured milk could improve colonic microflora through the reduction of the "auto-intoxication effect" of the colon. Today, this concept has been improved, and this field is now known as probiotics and prebiotics, defined as "a live microbial food supplement, that beneficially effects the host animal by improving its intestinal microbial balance" and "non-digestible food ingredients that benefit the host by selectively stimulating the growth or activity of one or a number of bacteria in the colon". A "symbiotic" is a combination of probiotics and prebiotics that "beneficially effects the host by improving the survival and implantation of live microbial dietary supplements in the gastrointestinal tract by selectively stimulating the growth of, and/or by activating the metabolism of, one or a number of health promoting bacteria".

The bacterial genera most often used in the field of probiotics are lactic acid bacteria, particularly *Lactobacillus* sp. and *Bifidobacterium* sp., these bacteria being important members of the gastrointestinal microflora of man and animals. Other microorganisms used as probiotics in humans include *Escherichia coli, Streptococcus* sp., *Enterococcus* sp., *Bacteroides* sp., *Bacillus* sp., *Propionibacterium* sp. and various fungi.

The external and internal surfaces of a human body are covered with bacteria. These organisms are traditionally referred to as "normal (friendly) flora", or symbionts with commensals. These friendly bacteria are involved in dynamic bio-film communications on the skin, mouth, naso-pharyngeal, intestinal and urogenital tracts, where the appropriate microflora exists. The human body depends on this friendly microflora: it helps in food digesting, produces vital vitamins and protects against various pathogens. The mechanisms by which probiotic microorganisms provide benefits for the internal and external surfaces of the host are numerous: competing with pathogens for food, preventing the adhesion of pathogens, antimicrobial activity, colonization resistance, various immune effects, adjuvant effect, antimutagenic effects, antigenotoxic effects, influence on enzyme activity, enzyme delivery and many others.

It is accepted that probiotics are usually targeted for use in intestinal disorders. The effectiveness of probiotics has been demonstrated in the prevention and treatment of a diverse spectrum of gastrointestinal disorders, such as antibiotic-associated diarrhea, infectious bacterial and viral diarrhea, etc. Some evidence suggests a role for probiotics in reducing the risk of colon cancer and the regression of tumors. For example, U.S. Pat. No. 5,308,615 by DeLoach and U.S. Pat. No. 5,478,557 by Nisbet describe a probiotic used for control of *salmonella*. Also, probiotics have been used therapeutically to lower cholesterol, to reduce blood pressure, treat rheumatoid arthritis, prevent cancer, and prevent or reduce the effects of atopic dermatitis, Crohn's disease, constipation as well as candidiasis and certain genitourinary tract infections such as bacterial vaginosis, vaginitis, or urinary tract infections. The immunomodualting action of probiotics is helpful in reduction of allergic reactions, stimulation of phagocytosis by peripheral blood leukocytes and secretory IgA, modulation of cytokine gene expression, and many other immunological effects.

PCT patent No. WO 00/75284 by Olshenitsky et. al. describes a probiotic composition comprising a volatile fraction of a plant extract prepared by steam distillation and suspended microorganism such as *E-coli*. *E-coli* is not exactly non-pathogenic and may cause some harm to humans in certain conditions. No fermentation process of medium ingredients with bacteria is described in arriving at the end product. Rather, evaporation and condensation is used which limits the end properties of the product. For example, without *E-coli* the product looses its antagonistic activity. Even with *E-coli* present, the antagonistic activity is limited because some pathogens can still grow in the medium during incubation for 24 hours.

Probiotic preparations currently on the market appear in various forms: in dairy products, processed into a product such as chewing gum, pills, capsules, etc., suspended in milk, freeze-dried or air-dried. They are generally composed of large numbers of one or more bacterial species that are common constituents of normal intestinal flora. Fermented milk (yogurt) and cheese are the most common foods with probiotics. U.S. Pat. No. 6,228,358 by Toba describes an antioxidation product made from fermented milk. Zhang describes red rice fermentation products in the U.S. Pat. No. 6,046,022. Other forms of probiotic preparations are freeze-dried or air-dried and they are available in tablets and in capsules. U.S. Pat. No. 5,702,927 by Murofushi describes bacteria containing xanthan gum. In some cases, probiotics have been suspended in an appropriate milieu for better survival. For example, U.S. Pat. No. 5,908,622 by Barclay describes growing of microflora in fermentation medium containing certain sodium salts. U.S. Pat. No. 6,294,166 by Hsia describes a method of stabilization of specifically dried bacterial compositions mixed with specific nutrients, yeast and soy protein, for long periods of time. Some authors, for example, U.S. Pat. No. 6,203,797 by Perry; U.S. Pat. No. 6,080,401 by Reddy; and U.S. Pat. No. 5,171,575 by Shibata, used various food/herb compositions with probiotics, without fermentation, to enhance medicinal effects.

Fermented cultures containing microorganisms can be used in other industries such as in cosmetics and pharmaceutical industry. U.S. Pat. No. 6,270,811 by Fregonese describes a composition containing a microbial culture for skin regenerating and removing scars and wrinkles.

Despite their health promoting effects, probiotics have only demonstrated short-term effects. In the study of the health effects of probiotics, the incidence and/or duration of acute, short term diseases, such as diarrhea, are frequently measured. The effects of probiotic bacteria on the incidence of diseases with a protracted etiology, such as cancer or heart disease, have generally not been measured. Moreover, the effects of probiotics in life-threatening diseases, such as cancer for example, are doubtful. For probiotics to have their therapeutic effect they should be used in high doses daily and the duration of their use should be sufficiently long.

Importantly, attention has been focused on the microorganisms per se, not their products of metabolism. Lactic acid fermentation is mainly considered for dairy products. Only in some oriental foods such as cassava, mixtures of grains and legumes, have lactic acid fermentation been used for the preparation of a variety of foods made from raw materials of plant and animal origin. Processed food tends to loose a substantial part of its useful components, ferments for example, as compared to raw materials.

U.S. Pat. No. 5,292,511 by Kim describes the lactic acid fermentation process being used for aloe preservation, and the end product used as a health-food supplement. The product and process described in the patent is limited in time (up to 96 hours) and temperature of fermentation (20–35 degrees C.). At 40 degrees C. the product is reported to start to decompose. The inventors of the present invention believe that the fermentation process is not complete from the point of view of the instant invention.

U.S. Pat. No. 4,298,620 by Hagiwara proposes a fermentation process for obtaining a fermented tear grass product combining a water extract of tear grass with a Lactobacillus strain, and foods and feeds comprising that product. This patent is incorporated herein in its entirety. Importantly, one critical step in the process as described in this patent is heating of the tear grass before fermenting it. In our opinion, this step effectively damages all useful ferments contained in the grass and significantly reduces its effectiveness. Also, since the number of bacteria is not reduced at the end of cultivation, the acidity of the end product (as measured by concentration of lactate) is low at about 0.7 to 3%. Another limitation is the typical addition of sugar at the end of cultivation. Finally, a heat sterilization process at 80 degree C. for 40 minutes effectively destroys all live microorganisms and active ingredients, ferments for example.

Other fermentation patents of interest include U.S. Pat. No. 5,219,597 by Mok; U.S. Pat. No. 5,700,684 by Ehret; U.S. Pat. No. 6,156,320 by Izvekova; U.S. Pat. No. 5,556,785 by Kishida; U.S. Pat. No. 5,747,020 by Rutherford; U.S. Pat. No. 4,407,828 by Raccach; U.S. Pat. No. 3,963,835 by Gryczka; U.S. Pat. No. 4,018,650 by Busta; U.S. Pat. No. 4,528,199 by Moon; U.S. Pat. No. 4,579,740 by Matrozza; U.S. Pat. No. 4,897,350 by El-Megeed; U.S. Pat. No. 4,749,652 by Robinson; U.S. Pat. No. 4,816,267 by Oka; U.S. Pat. No. 4,855,147 by Yokota; U.S. Pat. No. 4,579,739 by Darbyshire; U.S. Pat. No. 4,664,919 by Yan; U.S. Pat. No. 4,770,882 by Ingouf; and U.S. Pat. No. 3,944,676 by Fridman. They depict mostly various fermentation processes that are somewhat similar to the subject of the invention but in most cases these processes are short-term or carried out at low temperatures in solid phase and therefore incomplete from the point of view of the present invention.

One probable reason for limited effectiveness of probiotics in general is because of poor binding of the active microorganisms to the internal linings or external surface of the human body. Bacteria, especially in the state of freeze-dried suspension, have only limited time to develop a bond with the host. It takes several hours for the bacteria to become active after being consumed. Therefore, the bacteria are frequently expelled by natural processes such as digestion without allowing it to bond to the intestines and to produce enzymes, vitamins, amino acids, organic acids and other products of their metabolism. It is these metabolic products that represent the ultimate goal of the application of microorganisms. Live microorganisms might have a better chance to remain on the surface and tissue lining and attach thereto.

The need therefore exists for a medium containing live microorganisms as well as their metabolic products in high concentrations. Its application for humans is believed to be more effective and provide long-term benefits than the presently known suspensions of such microorganisms mostly in inactive state, even consumed in a high concentration.

SUMMARY OF THE INVENTION

It is an object of the present invention to provide a composition for a biologically benign medium containing non-pathogenic microorganisms and their metabolic products, such as enzymes with high proteolytic activity, vitamins, amino acids, low molecular weight proteins, organic acids, microelements and others.

It is another object of the invention to provide a fermented medium allowing the microorganisms to remain alive in active state so that better conditions are created for attachment thereof to the appropriate tissue of the host.

A further object of the present invention is to provide a medium of high acidity, at least above 3% of lactate concentration (>300 T°), to promote higher vitality of those microorganisms that survive in the process of natural selection in a harsh for them acidic environment. It is noted here that lactate also plays a role of a preservative for the medium of the invention.

It is another object of the invention to provide such medium based on raw natural fish, animal, and plant products not subjected to heavy food processing or application of heat to retain and preserve original ferments and other useful ingredients.

It is another object of the invention to provide a method for producing such medium. A further object is to provide a process of deep fermentation of the medium with appropriate microorganisms to cause production of metabolic products useful for human beings.

It is a further object of the present invention to provide methods of use of the medium of the invention in medicine, food, cosmetics, and other industries.

It is a further yet objective to provide a medium capable of producing long-term therapeutic effects on a human being or an animal.

In accordance with the present invention, a new symbiotic multi-component fermented hydrolyzed medium is provided with a broad spectrum of antibacterial, antiviral and antifungal properties, and antagonistic activity against Protozoa.

The medium is produced with non-pathogenic microorganisms, and has a high concentration of aromatic organic acids such as lactate, acetate, propionic, and other organic acids as metabolic end products of the fermentation process. The medium of the invention contains live non-pathogenic microorganisms in low concentrations and the products of their intensive metabolism, thereby keeping microorganisms in their most active alive condition. It is also believed that the bacteria that remain alive have more vitality, due to the natural selection of those that can survive in the environment of high acidity.

Non-pathogenic microorganisms genera used are Lactobacilli, Bifidobacteria, Acetic and Propionic bacteria, yeasts and food-grade fungi.

According to the invention, the fermentation process for obtaining sour-milk hydrolyzed medium is as follows. Initial ingredients include certain raw or dried vegetables, fruits, berries, offal, fish, eggs, plants, herbs, mash, sprouted grains and beans, aquatic plants, products of beekeeping, sea products, mushrooms, proteolytic ferments, chemicals and various types of sugar in the appropriate amounts. The ingredients are mixed in predetermined proportions and fermented with non-pathogenic bacteria or yeasts and certain food-grade fungi in milk or whey. Fermentation can also take place in water or another appropriate biocompatible liquid. The fermentation process takes 3–14 days (preferably 5–10 days) at 10–58 degrees C. (preferably 32–47 degrees C.) and can be carried out both aerobically and anaerobically. Typically, sour milk hydrolyzed medium includes about $10^5$ to $10^6$ live bacteria/yeasts cells per 1.0 g of product, and comprise 1 to 30 percent by weight of protein, all essential amino acids (resulting from the partial proteolysis of proteins during culturing), organic acids, microelements and vitamins. The acidity of the final product is about 300 to 900 T°, preferably between 500 to 800 T°, which corresponds to lactate concentration of between about 4.5% and 8%, and pH ranges from 1.5 to 6.5, preferably from about 3 to 4. There is no heat processing or pasteurization used in preparation of the medium.

The medium of the invention is not toxic and quite safe, and can be successfully utilized in high-risk patients, such as the elderly, hospitalized and the immunocompromised, including AIDS patients. No side effects were observed in babies or pregnant women in our studies.

The efficacy of the medium of the invention is comparable to modern pharmacological drugs (antibiotics, and antiviral and anti-fungal compounds). Moreover, this medium was effective against life-threatening diseases, such as cancer, tuberculosis, HIV/AIDS, and others, where traditional pharmacological drugs failed. No drug interaction was observed between pharmacological drugs and the medium of the present invention. On the contrary, the medium reduced considerably the side effects caused by toxic pharmacological drugs.

The medium can be used in food industry during the production of dairy products and cheese to accelerate cheese ripening and maturation, and as a method to cultivate and store for a long time in their most active condition Lactobacilli, acetic, propionic and bifidobacteria.

This medium can be used on farms as a feed supplement in animal husbandry for the prevention and treatment of infection diseases and to promote growth.

The medium of the invention can be used in cosmetic to improve skin condition (increasing skin elasticity and regeneration), to reduce and remove hems, scars and wrinkles, for healing burnt skin and as cream for sunburn.

The medium was found to possess a broad spectrum of therapeutic potential (the application was not limited to only GI tract) including reduction of DNA damage of the host cells. Boosting the immune system, immunomodulation, normalization of the number and function of blood cells, especially lymphocytes, are the most pronounced effects of this medium. These effects appear to be mainly caused by the end products of bacteria's metabolism.

Methods of administration of medium of the invention, in addition to accepted oral and intravaginal administration, include: 1) the external application to the skin as a bandage to the effected organs or coating the body (rubbing it into the skin), mostly the trunk and lymph nodes, 2) inhalation, 3) administration rectally via a retention enema, 4) dripping into the nose and ears, 5) intravenous injections for reducing infections and/or for intravenous nutrition, and 6) intraperitoneal injections for reducing infections.

The above and other objects, aspects, features and advantages of the invention will be more readily apparent from the description of the preferred embodiments thereof taken in conjunction with the appended claims.

DETAILED DESCRIPTION OF THE PREFERRED EMBODIMENTS

The first most important and unique aspect of the present invention is providing temperature and time conditions for the process of fermentation which ensure that at the end the fermentation is deep and complete. We found that generally at a point of about three days into the process of fermentation, most pathogens are destroyed/replaced. The medium of the present invention has to be fermented for at least 3 and preferably 5 to 14 days at a temperature of at least 10 and preferably 35 to 58 degrees C. to make sure that no pathogens are present. Another objective for this long time and higher temperature (as opposed to what is described in the prior art) is to make sure that microorganisms have adequate conditions to release products of their metabolism into the medium. By the end of the process, the medium has high acidity (generally, from 300 to 900 T°), low pH (from 1.5 to 6.5), high concentration of the metabolic products and relatively low concentration of microorganisms (from $10^5$ to $10^6$ cells/ml) as opposed to the preparations described by others.

In the most basic form, the medium of the invention can be prepared following these steps:

1. Provide a food product of plant nature, wash it and cut into small pieces (dimension of pieces can vary from about ½ millimeter to 4 centimeters). Juice extractor may be used for such purpose. The smaller the pieces are, the better hydrolysis will be achieved. A wide variety of food or plant products may be used, for example most fruits, vegetables, berries and herbs.

2. Provide a biocompatible liquid such as water, juice, etc. Most preferably, whey or milk or their combination may be used. Lemon, orange, or grape juice is another preferred biocompatible liquid.

3. Mix the food ingredient with the liquid ingredient in proportions of about 10–90% liquid to about 70–5% food by weight.

4. Add sugar to this mixture at about 0.1–30% by weight. Mix thoroughly and place in a thermostat for about 5–14 days at 32–58 degrees C.

Ambient microorganisms cause fermentation to proceed. For whey and milk, it is a naturally present Lactobacillus. Optionally and to better control fermentation, appropriate strain of microorganism can be specifically added, *Lactobacillus bulgaricus* for example.

The fermentation endpoint is determined by measuring the acidity in Terner degree. A satisfactory acidity for the medium is between 300 and 900 T°, and pH ranges between 1.5 to 6.5.

The strength and quality of the fermented medium of the invention depends on the number and nature of various ingredients and their proportions. Another unique aspect of the invention is to provide ingredients with high concentration of proteins such as tissue and organs of fish, poultry, animals and others. Offal ingredients are most preferred. As such, the second preferred method of producing the medium of the invention comprise providing at least one food/plant ingredient such as a vegetable, fruit, berry or herb as described above and one high protein ingredient such as an offal component, mushroom, sea product (fish, mussel, plankton for example), egg or nut. Proportion for plant with high protein ingredient and liquid is ranging from 15–80% solids to 20–85% liquid. In comparison to the first embodiment, the processing parameters may be opened up somewhat without compromising the completeness of the fermentation process and achieving high acidity at the end. The temperature range in this case is about 10 to 58 degrees C. and the time range is 3 to 20 days. It is still preferred to maintain higher temperature of about 32 to 47 degrees C. and ferment the medium for at least 5 days so the acidity reaches a level above 300 T°.

According to the third preferred embodiment and to achieve maximum strength, the composition of and preparation process for the medium of the invention are described in the following steps:

1. Provide for sprouting of at least one grain such as rye, lentil, wheat or barley, and beans for 2–6 days at 20–30 degrees C. in humid air. At the end of this period, grains can be optionally seeded with food-grade fungi such as *Aspergillus niger* and/or *Aspergillus orizae* to increase proteins concentration.

2. Inoculate a biocompatible liquid such as sterile milk or whey for 1 to 24 hours at 20–35 degrees C. with at least one of selected non-pathogenic microorganisms such as bacteria/yeasts. The number of live bacteria at this point is in the general range of from about $10^7$ to $10^9$ per ml of liquid, and pH is maintained close to neutral. Optionally, fermentation in water or juice can also be used.

Examples of non-pathogenic bacteria that can be used for the medium of the invention include, but not limited to, all strains of Lactobacilli, Bifidobacteria, Streptococci, Pedicocci, Leuconostoc, Propionic and Acetic bacteria. The yeast is Brewer's or Baker's yeast, which is added in active or non-active form (dried, autolyzed, hydrolyzed or extract). These non-pathogenic bacteria/yeasts can be alternately added without inoculation, immediately after the mixing of the various ingredients according to step 4. In this case however, fermentation will require more time.

Preferred strains of lactobacilli to be used in the medium of the invention include, but not limited to, *lactobacillus acidophilus, lactobacillus bifudus, lactobacillus brevis, lactobacillus bulgaricus, lactobacillus delbrucki, lactobacillus casei, lactobacillus cellobiosus, lactobacillus fermentum, lactobacillus gasseri, lactobacillus germentum, lactobacillus helveticus, lactobacillus johnsonii, lactobacillus lactis, lactobacillus leichimanii, lactobacillus plantarum, lactobacillus reuteri, lactobacillus rhamnosus, lactobacillus sake, lactobacillus salivaroes, lactobacillus thermophilus* and *lactobacillus xylosus*.

Preferred strains of Bifidobacteria include *Bifidobacterium adolescentis, Bifidobacterium bifidum, Bifidobacterium breve, Bifidobacterium cereus, Bifidobacterium infantis, Bifidobacterium lactis, Bifidobacterium longum,* and *Bifidobacterium thermophilus*.

Streptococci strains to be used include preferably *Streptococcus lactis, Streptococcus cremoris, Streptococcus diacetylactis, Streptococcus thermophilus,* and *Streptococcus faecium*.

Preferred yeast includes *Saccharomyces boulardii, Saccharomyces cerevisiae,* and *Saccharomyces lactis*.

Propionic bacteria strain is preferably *propionibacterium shermanii*.

Pedicocci strains that may be used in the present invention include *Pediococcus cerevisia, Pediococcus acidilactici* and *Pediococcus pentosaceus*.

Leuconostoc strains include *Leuconostoc cremoris, Leuconostoc dextranicum,* and *Leuconostoc mesenteriodes*.

3. Provide other ingredients as specified below to include at least one type of dried or preferably fresh vegetables, fruits, berries, offal, and herbs, all thoroughly washed with water in addition to a product of beekeeping, mash, and proteolytic ferments. All products, including sprouted grains, should be homogenized/pulverized or mechanically processed, for example through juice extractor. In case of dried products, their amount should be 3–5 times less by weight, they should be soaked in an appropriate volume of water for some time (for minutes or hours depending on type of product) to produce the same quantity of mass as when using fresh ingredients.

Vegetables preferably used are of leaf and root types e.g. various cabbages, beets, rutabaga, carrot, pumpkin, spinach, beet, watermelon, melon, peanut, artichoke, eggplant, pepper sweet, asparagus, and tomato. Fruits to be preferably used are apples, pears, kiwi, plums, citrus, apricots, grapes/raisins, mango, guava, bananas, biwa, cornel, fig, cherry plum, quince, peach, pomegranate, avocado, pineapple, date, papaya. Berries preferably include raspberry, bilberry, guelder rose, dog rose, ash berry (red and black), currant (red, black, and white), sea-buckthorn berries, gooseberry, schizandra, blackberry, cowberry, bird cherry, cranberry, sweet cherry, cherry, and strawberry. Preferred herbs and their roots are ginseng, celery, parsley, dill, dandelion, nettle, ginseng, and spinach. Preferred high protein products are offals including spleen, kidney, heart, liver, brains, maw, and stomach as well as mushrooms, sea products (fish, mussel, plankton for example), eggs or nuts. Preferred products of beekeeping are propolis, honey, royal jelly, and pollen of flower.

4. Mix the preferred composition of the above ingredients as follows: 25 to 80% by weight of inoculated milk or whey, 1 to 30% by weight of vegetables, 1–20% by weight of fruits, 1–20% by weight of berries, 1–15% by weight of herbs, 1–30% by weight of high protein ingredients, 0.1–5% by weight of products of beekeeping, 1–10% by weight of sprouting grains and beans, 1–15% by weight of mash, 0.1–1.0% by weight of proteolytic ferments (pepsin or alike).

5. Provide specified amount of sugar, 0.1–30% by weight, and thoroughly mix into the medium. Preferred types of sugar include glucose, fructose, sucrose, mannose, maltose, galactose, raffinose, corn syrup, lactose or other mono-, di- or polysaccharides, which can be utilized by Lactobacilli or Bifidobacteria. These sugars can be used both in combination and alone.

6. Provide at least one of the following chemical compounds: potassium, sodium, magnesium, calcium, trace of cobalt, trace of manganese, and alcohol. The chemical compounds should be dissolved in water and added to the mixture. Optionally, horns and hoofs can be used, but this might worsen the taste of the product.

7. Ferment all of the above ingredients aerobically or anaerobically for 3–20 days at 10–58 degrees C. It is preferred to ferment the mixture for 5–10 days at 32–47 degrees C.

8. After fermentation, separate the liquid (for example by filtering of with a centrifuge), which constitutes the desired sour milk hydrolyzed medium of the invention. The number of live bacteria in the liquid medium at the end of fermentation is about $10^5$ to $10^6$ per one gram of liquid. The removed sediment contains all the useful ingredients as well and the same bacteria and can be used as feed supplement for human consumption and in animal husbandry. The sediment can be alternatively lyophilized at room temperature and stored for later consumption.

The resulting products, sour milk hydrolyzed medium and sediment, can be stored at room temperature for several months. When refrigerated at 2–15 degree C., it can last for up to several years without deterioration. No preservatives need to be added.

The acidity of the final liquid medium product is about 300 to 900 T°, preferably between 500 to 800 T°, which corresponds to lactate concentration of between about 4.5% and 8%, and pH ranges from –1.5 to 6.5, preferably from about 3 to 4.

The products of the suggested fermentation process are not toxic and have application in medicine, food industry, biotechnology, veterinary, animal, poultry, and fish husbandry, athletic sport as a food supplement, and/or therapeutic drugs and can be used as a prophylactic agents against diseases. The medium was observed to be non-toxic, even for challenging groups of patients such as the elderly, hospitalized and the immunocompromised, including AIDS patients, expecting mother and babies. The most pronounced effects of the medium of the present invention include immunomodulation, improving physiologic function at the cellular level, for various organs and the entire body. The medium of the invention has a broad spectrum of antimicrobial activity with the ability to destroy and/or inhibit growth of many different species of pathogenic organisms.

Methods of administration of the medium of the invention depend on the specific condition. For general application, oral administration is useful. Other applications include: 1) the external transcutaneous application as a bandage soaked in the medium placed over the skin above effected organs or coating the body (rubbing it into the skin), mostly the trunk and particularly lymph nodes, 2) inhalation, especially for breathing disorders, 3) administration rectally via a retention enema, 4) dripping into the nose and ears, 5) intravenous injections (after removal or microorganisms via known means such as through a filter) for reducing infections and/or for intravenous nutrition, 6) intraperitoneal injections for reducing infections, and 7) intravaginally via a soaked tampon.

A proper dosage of the medium and sediment of the present invention in humans depends upon the particular needs. In case of a life threatening condition, the application of the medium of the invention should be the most aggressive and combine several possible routes of administration. As an example, an AIDS patient should take the medium of the invention orally 2–3 times a day at any time in the amount of about 1 to 2 ml/kg of body weight in addition to coating the body with the medium as much skin area as possible, especially lymph nodes, 1 to 2 times a day, in the morning and at night. In case of liver, kidney, pancreas, etc. intoxication caused by HAART, skin bandages soaked with the medium should be placed over the skin above effected organs 1–4 times a week. In case of lung problems, additional inhalation on a daily basis is needed as well. Our evaluation showed that all lung infections in AIDS patients disappeared within 1–3 weeks. Additionally, rectal administration, typically with oil, should be used 3–5 times a week. Women should use intravaginal tampons at least 2–4 times a week for up to 2 hours at a time. Our studies demonstrated that as a result of such intensive therapy, opportunistic infections resolved mostly within 2–8 weeks, CD4 increased by 20–30 cells/month, accompanied with increasing CD8 and ratio CD4/CD8. After 1–4 months of such therapy, it can be interrupted for 1–3 weeks or the doses and/or number of methods of administration can be reduced. For a less serious condition, oral administration is generally enough.

The hydrolyzed fermented medium of the invention is effective in treating a variety of infectious viral diseases including Hepatitis A, B, and C; myxoviruses and influenza; herpes of various types; virus of poliomyelitis; adenoviruses; various types of encephalitis; proteus, and foot-and-mouth disease. The medium is effective in treating human immunodeficiency virus (HIV) and AIDS. It can be used for Ebola, smallpox, Congo-Crimean hemorrhagic fewer, and yellow fewer.

Bacteria caused infections can also be treated with the medium of the invention and include tuberculosis; leprosy; cholera; various forms of meningitis and Legionnaire's disease; syphilis; gonorrhea; Lyme disease; typhus; various Streptococcuses and Staphylococcuses; anthrax; botulism; diphtheria; gangrene; tetanus; tularemia; chamydiae; plague; mycoplasmas; pathogenic *E-coli*; etc. The medium is also effective in treating septic shock, toxic shock, and multiple organ failure.

The medium of the invention is also effective against various fungi including *Candida, Pneumocystis*, and various other lung infections.

The product of the invention is effective for Protozoa including various types of Plasmodium of malaria; Leishmaniasis; various Trypanosomas; Cryptosporidium, Toxoplasmosis, and Isospora, as wells as against various parasites of cattle. It can be successfully used against helminth infections.

The medium is useful in treating cancer including advanced cancer such as bladder cancer, breast cancer, colon cancer, gastrointestinal cancers, head and neck cancers, kidney cancer, leukemia, lymphogranulomatosis, liver cancer, lymphoma, lung cancer, prostate cancer, ovary cancer, skin cancers, thymus cancer, thyroid cancers, tongue cancer, vagina cancer and uterus cancer.

The medium is found to be effective for cardiovascular diseases including various insults and strokes (including paralysis); myocardial infarction including the use as a prophylactic agent and after infarction for patient recovery; cerebral thrombosis; myocarditis and aneurysms; ischemia; arteriosclerosis; coronary artery disease; hypertension; rheumatism; various abnormalities of blood coagulation system.

Another area of use in medicine is for kidney and liver diseases including dialysis; pyelonephritis, kidney colic; stones in kidney and liver; hemolytic jaundice.

Of course, the medium can be used for a broad range of digestion diseases: for gastrointestinal diseases including dysbacteriosis, dyspepsia, irritable bowel syndrome, insomnia, etc; various forms of diarrhea including helicobacter pylori, clostridium difficile, diarrhea induced by cholera, AIDS, rotavirus, antibiotic-associated, etc.; for inflammatory bowel diseases such as Crohn's disease, ulcerative colitis, GI Ulcers, etc.

Use in transplantation of organs is another area of interest. Good results were observed when the medium was used after the transplantation of kidney and gut; donor organs were not rejected. In many cases, patients avoided the need for transplantation after treatment with the medium of the invention.

The medium found use in treating neurodegenerative diseases, including Alzheimer's Disease/Dementia; Parkinson disease; encephalopathy; and sclerosis.

This medium can be also used for autoimmune diseases (arthritis, polyarthritis, and rheumatoid arthritis), to reduce inflammation, and allergies of various etiologies.

The medium is effective against excessive radiation, both ionizing (including lethal total body) and ultraviolet. It can be used for healing wounds and for bone fractures. It was very successfully used in surgical patients.

Further areas of medical use include diabetic conditions; to improve general physical and mental abilities and endurance; for hypoxia, decompression disease; for healing skin in burn patients; alcoholic and drug abuse; hematoma resorbtion; for sexual dysfunctions and sexual diseases (vaginitis, urethritis, bladder infection, etc.); for relief of side effects of menopause; for treating endometriosis; psoriasis; bronchitis; all types of pain including chronic pain; gingivitis and parodontosis; atrophy; dystrophy; omphalitis, otitis, sinusitis, and rhinitis; and for reduction in cholesterol level.

The medium of the invention can be used both alone and in conjunction with pharmaceutical drugs as adjuvant therapy. The administration of the medium reduces considerably the toxic side effects of conventional therapy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for producing a fermented hydrolyzed medium containing non-pathogenic microorganisms and products of their metabolism comprising the steps of:
   a) providing at least one solid food ingredient reduced to small pieces;
   b) providing at least one biocompatible liquid ingredient containing at least one non-pathogenic microorganism;
   c) mixing said solid food ingredient with said biocompatible liquid ingredient thereby obtaining a mixture in proportions of about 10–90% liquid to about 70–5% solid food by weight;
   d) adding a sugar by mixing the sugar into the mixture at about 0.1–30% by weight; and
   e) fermenting the mixture at 10–58 degrees C. until acidity reaches at least about 300 degree Turner; whereby obtaining high acidity medium with high concentration of microorganisms and products of their metabolism.

2. The method of claim 1, wherein said solid food ingredient is a plant.

3. The method as in claim 2, wherein said plant is selected from the group consisting of vegetables, herbs, grains, and fruits.

4. The method as in claim 1, wherein said biocompatible liquid ingredient is selected from the group consisting of water, juice, milk, whey, and combination of whey and milk.

5. The method as in claim 1, wherein said non-pathogenic microorganism is a non-pathogenic bacteria or yeast.

6. The method of claim 5, wherein said non-pathogenic bacteria are selected from the group consisting of *Lactobacilli, Bifidobacteria, Streptococci, Pediococci,* Leuconostoc, Propionic and Acetic bacteria.

7. The method of claim 6, wherein said *Lactobacilli* are selected from the group consisting of *Lactobacillus acidophilus, Lactobacillus bifidus, Lactobacillus brevis, Lactobacillus bulgaricus, Lactobacillus delbrucki, Lactobacillus casei, Lactobacillus cellobiosus, Lactobacillus fermentum, Lactobacillus gasseri, Lactobacillus germentum, Lactobacillus helveticus, Lactobacillus johnsonhii, Lactobacillus lactis, Lactobacillus leichimanii, Lactobacillus plantarum, Lactobacillus reuteri, Lactobacillus rhamnosus, Lactobacillus sake, Lactobacillus salivaroes, Lactobacillus thermophilus* and *Lactobacillus xylosus.*

8. The method of claim 6, wherein said *Bifidobacteria* are selected from the group consisting of *Bifidobacterium adolescentis, Bifidobacterium bifidum, Bifidobacterium breve, Bifidobacterium cereus, Bifidobacterium infantis, Bifidobacterium lactis, Bifidobacterium longum,* and *Bifidobacterium thermophilus.*

9. The method of claim 6, wherein said *Streptococci* are selected from the group consisting of *Streptococcus lactis, Streptococcus cremoris, Streptococcus diacetylactis, Streptococcus thermophilus,* and *Streptococcus faecium.*

10. The method of claim 1, wherein said solid food ingredient is a solid plant, said step (a) further including providing a high protein ingredient reduced to small pieces, said step (c) including mixing said plant, high protein, and liquid ingredients with sugar in proportions by weight of about 20–85% liquid to 15–80% solids, and said fermenting step (e) carried out for 3 to 14 days.

11. The method of claim 10, wherein said plant ingredient is selected from the group consisting of vegetables, herbs, berries, grains, and fruits.

12. The method of claim 10, wherein said high protein ingredient is an offal product.

13. The method of claim 10, wherein said high protein ingredient is a sea product.

14. The method of claim 10, wherein the step (e) of fermenting is conducted at a temperature of about 35–47 degrees C. for about 3–14 days.

* * * * *